(12) United States Patent
Dickson

(10) Patent No.: US 7,575,601 B2
(45) Date of Patent: Aug. 18, 2009

(54) LOCKING EXPANDABLE IMPLANT AND METHOD

(75) Inventor: Andrew M. Dickson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 290 days.

(21) Appl. No.: 11/412,556

(22) Filed: Apr. 27, 2006

(65) Prior Publication Data

US 2007/0255421 A1    Nov. 1, 2007

(51) Int. Cl.
*A61F 2/44* (2006.01)
(52) U.S. Cl. .................................... 623/17.15
(58) Field of Classification Search .............. 623/17.15, 623/23.47
See application file for complete search history.

(56) References Cited

U.S. PATENT DOCUMENTS

| | | | |
|---|---|---|---|
| 2,333,033 A | 10/1943 | Mraz | |
| 3,701,605 A * | 10/1972 | Yoshio | ........................ 402/58 |
| 4,157,715 A | 6/1979 | Westerhoff | |
| 4,289,123 A | 9/1981 | Dunn | |
| 4,386,603 A | 6/1983 | Mayfield | |
| 4,401,112 A | 8/1983 | Rezaian | |
| 4,553,273 A | 11/1985 | Wu | |
| 4,554,914 A | 11/1985 | Kapp et al. | |
| 4,599,086 A | 7/1986 | Doty | |
| 4,636,217 A | 1/1987 | Ogilvie et al. | |
| 4,657,550 A * | 4/1987 | Daher | ..................... 623/17.11 |
| 4,892,546 A | 1/1990 | Kotz et al. | |
| 5,002,576 A | 3/1991 | Fuhrmann et al. | |
| 5,236,460 A | 8/1993 | Barber | |
| 5,281,226 A | 1/1994 | Davydov et al. | |
| 5,290,312 A | 3/1994 | Kojimoto et al. | |
| 5,336,223 A | 8/1994 | Rogers | |
| 5,405,391 A | 4/1995 | Hednerson et al. | |
| 5,413,602 A | 5/1995 | Metz-Stavenhagen | |
| 5,458,641 A | 10/1995 | Ramirez Jimenez | |
| 5,480,442 A | 1/1996 | Bertagnoli | |
| 5,571,192 A * | 11/1996 | Schonhoffer | .............. 623/17.11 |
| 5,658,335 A | 8/1997 | Allen | |
| 5,702,453 A * | 12/1997 | Rabbe et al. | .............. 623/17.16 |
| 5,702,455 A * | 12/1997 | Saggar | ..................... 623/17.15 |
| 5,723,013 A | 3/1998 | Jeanson et al. | |
| 5,776,197 A | 7/1998 | Rabbe et al. | |
| 5,776,198 A * | 7/1998 | Rabbe et al. | .............. 623/17.15 |
| 5,800,547 A | 9/1998 | Schafer et al. | |
| 5,916,267 A | 6/1999 | Tienboon | |
| 5,989,290 A * | 11/1999 | Biedermann et al. | ..... 623/17.11 |
| 6,015,436 A | 1/2000 | Schonhoffer | |
| 6,045,579 A | 4/2000 | Hochshuler et al. | |
| 6,080,193 A | 6/2000 | Hochshuler et al. | |
| 6,126,660 A | 10/2000 | Dietz | |
| 6,176,881 B1 | 1/2001 | Schar et al. | |
| 6,190,413 B1 | 2/2001 | Sutcliffe | |
| 6,193,755 B1 | 2/2001 | Metz-Stavenhagen et al. | |

(Continued)

FOREIGN PATENT DOCUMENTS

DE    20207853 U1 *  10/2002

*Primary Examiner*—David Isabella
*Assistant Examiner*—Ann Schillinger

(57) ABSTRACT

Embodiments of the invention include expandable, implantable devices and methods with a locking feature. Devices expand linearly to provide secure fixation between or among anatomical structures. In some embodiments, an implant replaces one or more vertebral bodies of the spine.

26 Claims, 4 Drawing Sheets

U.S. PATENT DOCUMENTS

| | | |
|---|---|---|
| 2002/0082695 A1 | 6/2002 | Neumann |
| 2002/0161441 A1 | 10/2002 | Lang et al. |
| 2003/0045877 A1 | 3/2003 | Yeh |
| 2004/0049271 A1 | 3/2004 | Biedermann et al. |
| 2004/0059271 A1 | 3/2004 | Berry |
| 2004/0153160 A1 | 8/2004 | Carrasco |
| 2004/0172129 A1* | 9/2004 | Schafer et al. ........... 623/17.11 |
| 2004/0181283 A1 | 9/2004 | Boyer, II et al. |
| 2004/0186569 A1* | 9/2004 | Berry ...................... 623/17.11 |
| 2005/0060036 A1 | 3/2005 | Schultz et al. |
| 2005/0090898 A1* | 4/2005 | Berry et al. ............... 623/17.11 |
| 2005/0113921 A1* | 5/2005 | An et al. .................. 623/17.11 |
| 2005/0234550 A1* | 10/2005 | Metz-Stavenhagen .... 623/17.11 |
| 2006/0058879 A1* | 3/2006 | Metz-Stavenhagen .... 623/17.15 |

* cited by examiner

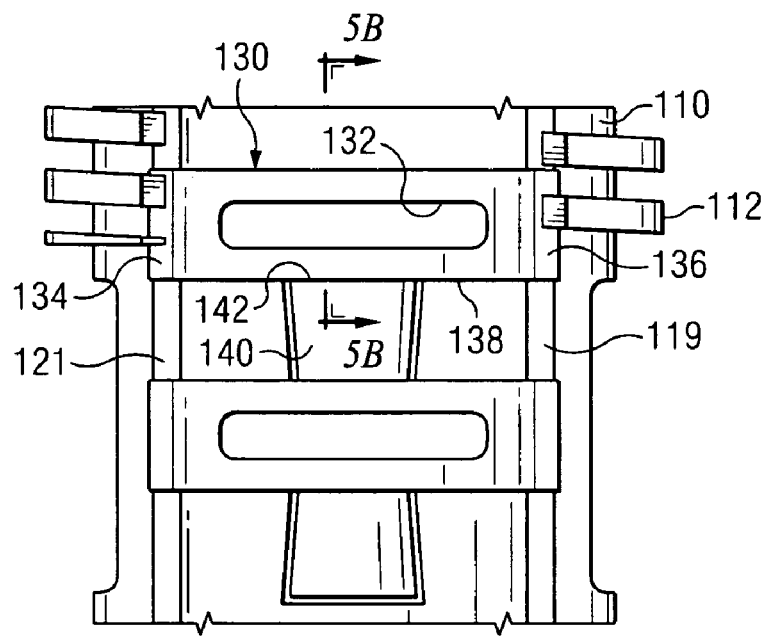
*Fig. 5A*
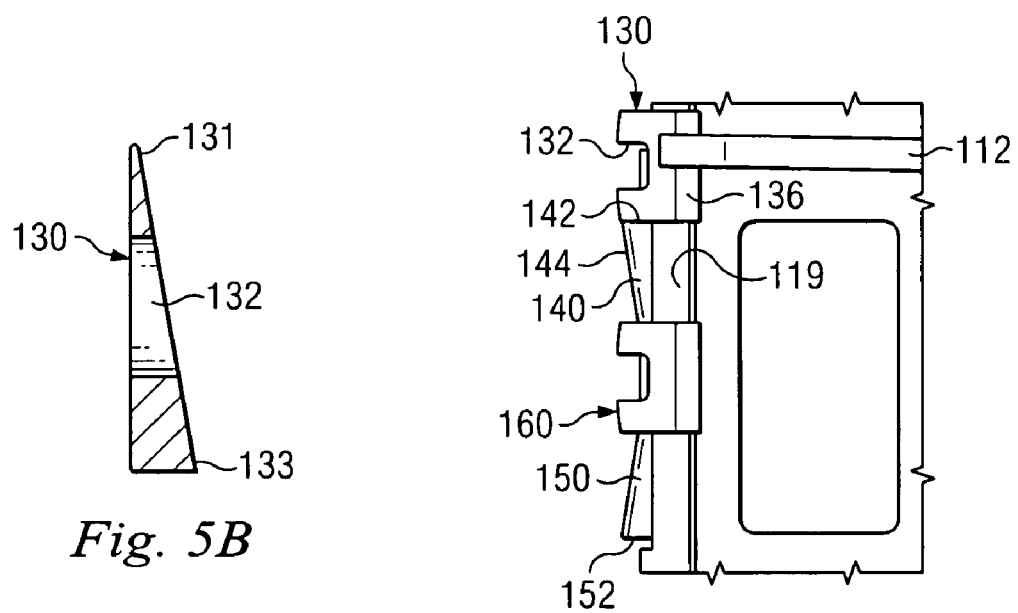
*Fig. 5B*
*Fig. 6*

LOCKING EXPANDABLE IMPLANT AND METHOD

FIELD OF THE INVENTION

The present invention relates generally to the field of replacing portions of the human structural anatomy with medical implants, and more particularly relates to an expandable implant and method for replacing skeletal structures such as one or more vertebrae or long bones.

BACKGROUND

It is sometimes necessary to remove one or more vertebrae, or a portion of the vertebrae, from the human spine in response to various pathologies. For example, one or more of the vertebrae may become damaged as a result of tumor growth, or may become damaged by a traumatic or other event. Excision of at least a generally anterior portion, or vertebral body, of the vertebra may be referred to as a corpectomy. An implant is usually placed between the remaining vertebrae to provide structural support for the spine as a part of a corpectomy. FIG. 1 illustrates four vertebrae, $V_1$-$V_4$ of a typical lumbar spine and three spinal discs, $D_1$-$D_3$. As illustrated, $V_3$ is a damaged vertebra and all or a part of $V_3$ could be removed to help stabilize the spine. If removed along with spinal discs $D_2$ and $D_3$, an implant may be placed between vertebrae $V_2$ and $V_4$. Most commonly, the implant inserted between the vertebrae is designed to facilitate fusion between remaining vertebrae. Sometimes the implant is designed to replace the function of the excised vertebra and discs. All or part of more than one vertebrae may be damaged and require removal and replacement in some circumstances.

Many implants are known in the art for use in a corpectomy procedure. One class of implants is sized to directly replace the vertebra or vertebrae that are being replaced. Another class of implants is inserted into the body in a collapsed state and then expanded once properly positioned. Expandable implants may be advantageous because they allow for a smaller incision when properly positioning an implant. Additionally, expandable implants may assist with restoring proper loading to the anatomy and achieving more secure fixation of the implant. Implants that included insertion and expansion mechanisms that are narrowly configured may also provide clinical advantages. In some circumstances, it is desirable to have vertebral endplate contacting surfaces that effectively spread loading across the vertebral endplates. Effective implants should also include a mechanism for maintaining the desired positions, and in some situations, being capable of collapsing. Fusion implants with an opening may also be advantageous because they allow for vascularization and bone growth through all or a portion of the entire implant.

Expandable implants may also be useful in replacing long bones or portions of appendages such as the legs and arms, or a rib or other bone that is generally longer than it is wide. Examples include, but are not limited to, a femur, tibia, fibula, humerus, radius, ulna, phalanges, clavicle, and any of the ribs.

SUMMARY

One embodiment of the invention is a medical implant expandable along a longitudinal axis. The implant in some embodiments is for supporting skeletal structures. Embodiments of the implant include a first tubular member with a connection end and an opposite skeletal interface end, the connection end of the first tubular member including an area with protrusions and an area without protrusions, and a second tubular member with a connection end configured to engage with the connection end of the first tubular member, the second tubular member having an opposite end opposite from the connection end of the second tubular member, the connection end of the second tubular member including an area with protrusions and an area without protrusions. In a first angular relationship between the first and second tubular members, the area with protrusions of the first tubular member slides longitudinally along the area without protrusions of the second tubular member, and in a second angular relationship the protrusions of the first and second tubular members engage to prevent longitudinal sliding between the first and second tubular members. Embodiments may also include an interference mechanism configured to enter at least a portion of the area without protrusions of the first tubular member to prevent angular movement between the first tubular member and the second tubular member.

An embodiment of the invention is an expandable medical implant for supporting skeletal structures. Some embodiments of the implant include a first tubular member with a connection end and an opposite skeletal interface end and a second tubular member with a connection end configured to engage with the connection end of the first tubular member, the second tubular member having an opposite end opposite from the connection end of the second tubular member. The embodiments may also include an interference mechanism with a first position that allows movement between the first tubular member and the second tubular member and a second position that prevents movement between the first tubular member and the second tubular member. The connection ends of the first tubular member and the second tubular member are configured to allow sliding translation between the first tubular member and the second tubular member when in a first angular relationship and to prevent sliding translation when in a second angular relationship in some embodiments.

Another embodiment of the invention is a method of implanting an expandable medical implant. The method embodiment may include positioning the expandable medical implant between skeletal structures, expanding the expandable medical implant by moving a first tubular member with a connection end and an opposite skeletal interface end longitudinally along a second tubular member with a connection end configured to engage with the connection end of the first tubular member, and rotating one or both of the first and second tubular members to change the angular relationship between the first and second tubular members and prevent sliding translation of the first tubular member longitudinally along the second tubular member. Embodiments may also include positioning an interference mechanism with a first position that allows movement between the first tubular member and the second tubular member and a second position that prevents movement between the first tubular member and the second tubular member into the second position.

Yet another embodiment of the invention is a method of implanting an expandable medical implant. The method embodiments may include positioning the expandable medical implant between skeletal structures and attaching a surgical instrument to a first tubular member, the first tubular member having a connection end and an opposite skeletal interface end longitudinally along a second tubular member, the second tubular member having a connection end configured to engage with the connection end of the first tubular member, the second tubular member having an opposite end opposite from the connection end of the second tubular member. Further embodiments may include attaching the surgical instrument to a third tubular member, the third tubular member having a connection end configured to engage with the opposite end of the second tubular member, the third tubular member having an opposite skeletal interface end, expanding the expandable medical implant by moving one or both of the first tubular member and the third tubular member longitudinally along the second tubular member to longitudinally lengthen the expandable medical implant, and rotating one or each of the first, second, and third tubular members to change the angular relationship among the first, second, and third tubular members and prevent sliding translation of the first and third tubular members longitudinally along the second tubular member. Embodiments may also include positioning a first interference mechanism with a first position that allows movement between the first tubular member and the second tubular member and a second position that prevents movement between the first tubular member and the second tubular member into the second position and positioning a second interference mechanism with a first position that allows movement between the third tubular member and the second tubular member and a second position that prevents movement between the third tubular member and the second tubular member into the second position.

In another aspect, the present invention provides a telescopic spacer. A first tubular member telescopingly receives a portion of a second member. In a first rotational alignment, the second member may be telescopingly positioned along the longitudinal axis. In a second rotational alignment, the first member is longitudinally fixed with respect to the second member. In one aspect, the first rotational alignment is oriented 90 degrees from the second rotational alignment. In another aspect, a third member telescopingly receives an opposite portion of the second member. These and other aspects of the present invention will become apparent from the following detailed description.

Further aspects, forms, embodiments, objects, features, benefits, and advantages of the present invention shall become apparent from the detailed drawings and descriptions provided herein.

BRIEF DESCRIPTION OF THE DRAWINGS

FIG. 5A is a partial elevation view of a central portion of the implant of FIG. 2A.

FIG. 5B is a partial cross-sectional view of the lock of FIG. 5A.

FIG. 6 a partial side elevation view of the implant of FIG. 5.

DETAILED DESCRIPTION

Figures 1, 2A:
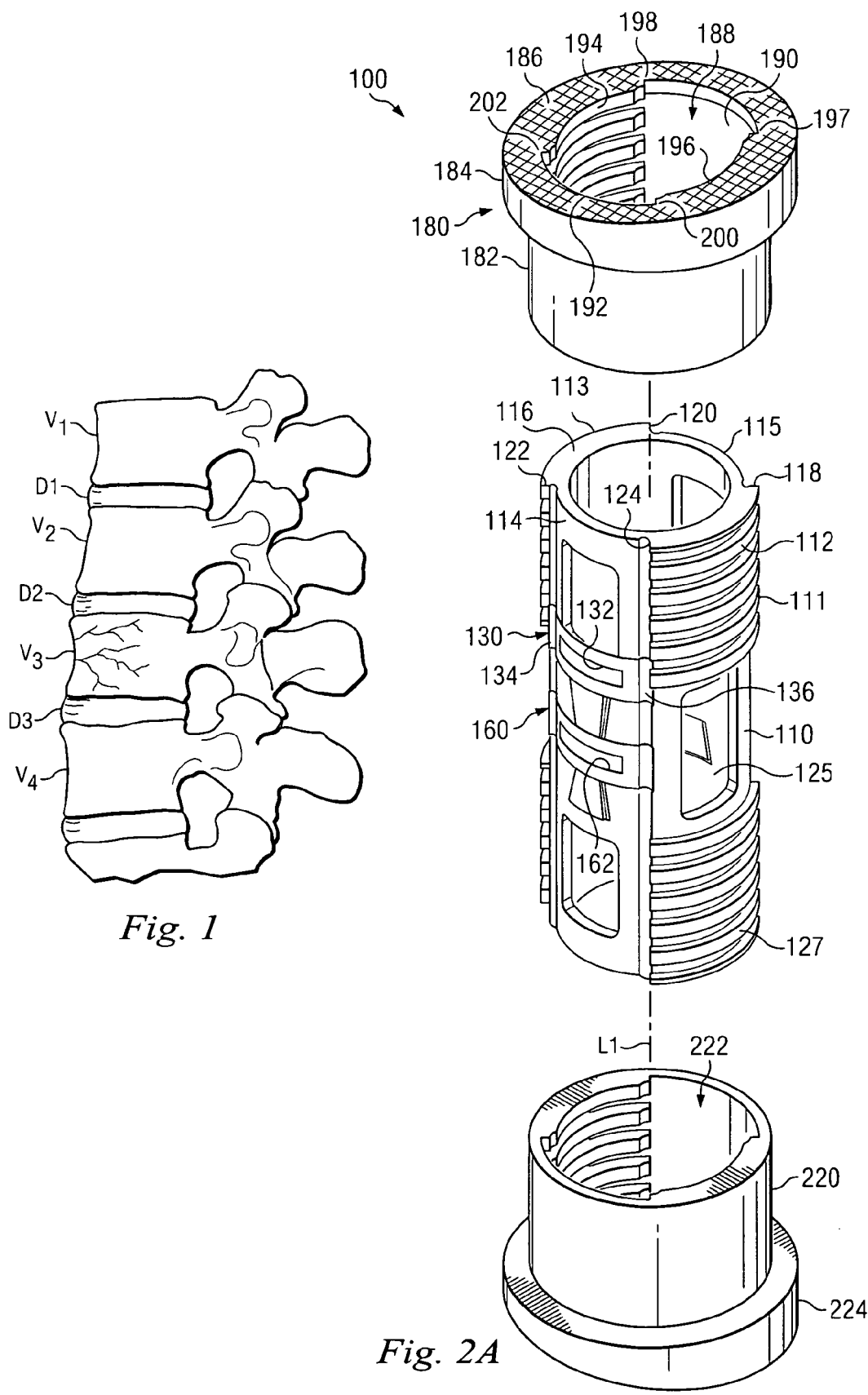
FIG. 1 is an elevation view of a segment of a lumbar spine.
FIG. 2A is an exploded perspective view of an expandable implant embodiment.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2B:
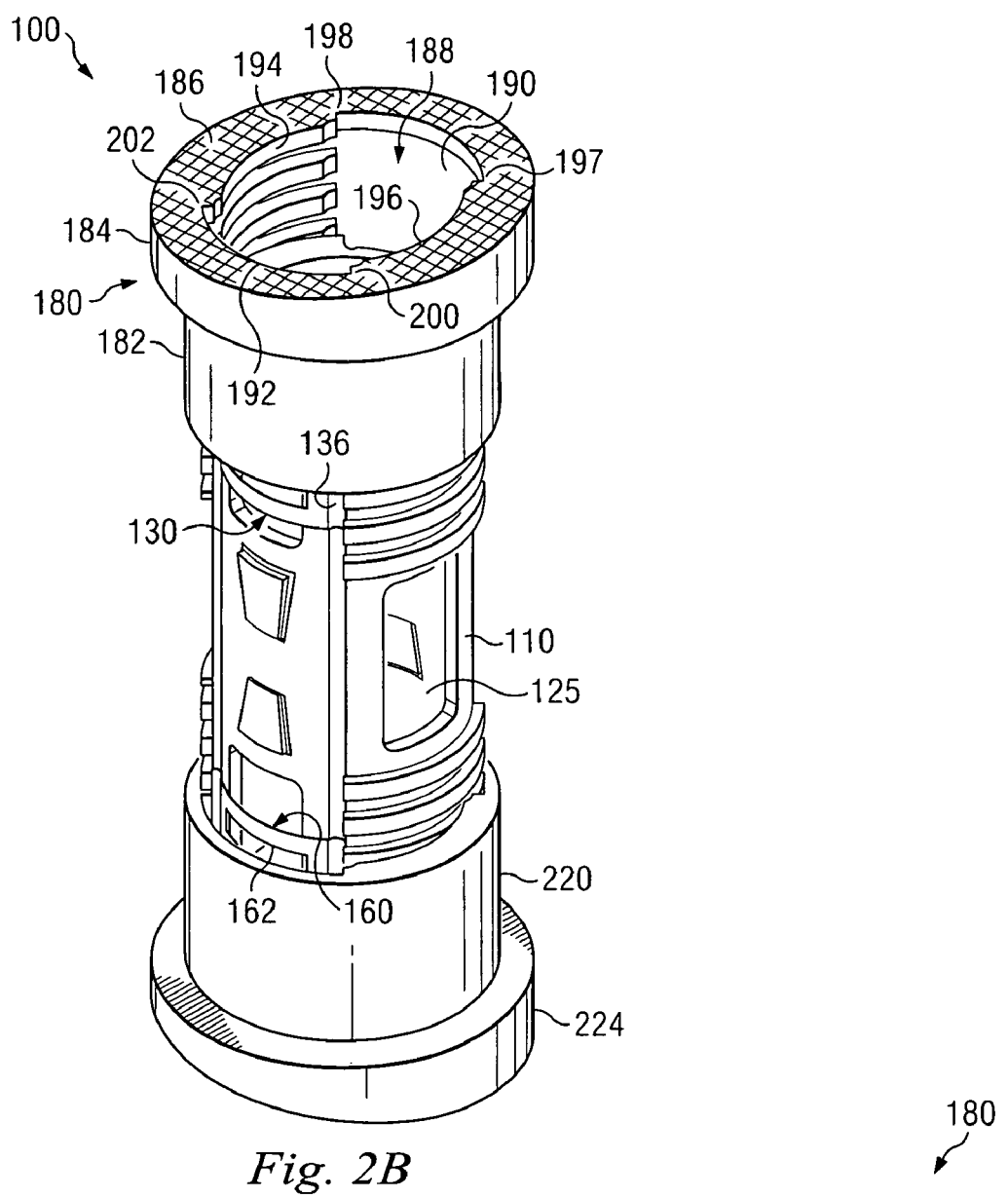
FIG. 2B is a perspective view of the assembled implant of FIG. 2A.

Referring now to FIGS. 2A and 2B, there is shown an expandable implant 100 in accordance with one aspect of the present invention. The expandable implant 100 includes a tubular main body 110 with an upper portion 111. Upper portion 111 includes a first helically threaded area 112 extending over approximately one-quarter of the outer circumference of the device and an opposing helically threaded portion 113 extending around substantially the same portion of the device. Threaded portions 112 and 113 are spaced from each other by unthreaded channels 114 and 115. In the illustrated embodiment, the helically threaded portions 112 and 113 have a thread crest diameter of a first dimension and the unthreaded areas 114 and 115 have a diameter slightly less than the root diameter in the threaded portions and significantly less than the first dimension of the thread crests. At the intersection between threaded portion 112 and unthreaded portion 115, there is a dovetail projection 118 formed along the longitudinal axis L1. Similarly, extending along the junction between unthreaded channel 115 and threaded portion 113 is a dovetail projection 120. On the alternate side of the device, a dovetail projection 122 extends between threaded portion 113 and unthreaded channel 114. In a similar manner, a dovetail projection 124 is formed along the longitudinal axis extending between the junction of unthreaded channel 114 and threaded portion 112. The main body 110 includes an upper end surface 116. The term "dovetail projection" as used herein includes at least any extension of material capable of capturing or being captured within an adjacent segment of material or separate component, and is not limited to walls of a specific shape. Lower portion 127 of the main body 110 has substantially the same features as described above with respect to upper portion 111 and will not be further described.

In one aspect, main body 110 includes a pair of locking tabs or wedge structures 140 and 150 centrally located near the mid-section of the main body. A similar pair of locking tabs, partially shown in FIG. 2A, are formed on the opposite side of the device. The height of the locking tabs is smaller adjacent to the midpoint of the main body and extends to a greater height from the surface of the unthreaded channel 114 as it extends distally away from the middle of the main body. Tab 140 includes an abutting shoulder 142 having a height extending above the outer surface of the main body and tapers to a decreasing height at central portion 144. Similarly, wedge 150 includes an abutting shoulder 152 as it extends away from the midpoint of main body 110. As shown more fully in FIG. 4B, main body 110 includes a pair of longitudinally extending, semi-circular grooves 119 and 121 defined within the outer surface. Grooves 119 and 121 are formed at the juncture between the threaded portions and the unthreaded portions. Grooves similar to 119 and 121 are formed on the opposing exterior surface of the device.

Figure 4A:
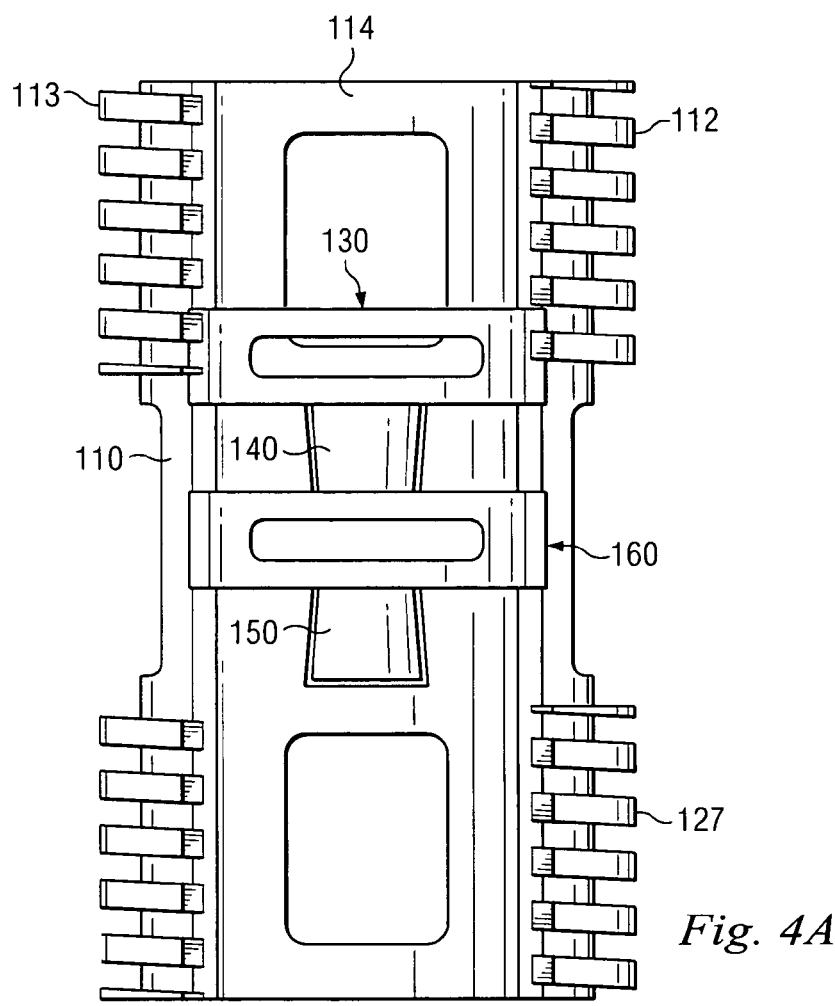
FIG. 4A is an elevation view of a central portion of the implant of FIG. 2A.
Figure 4B:
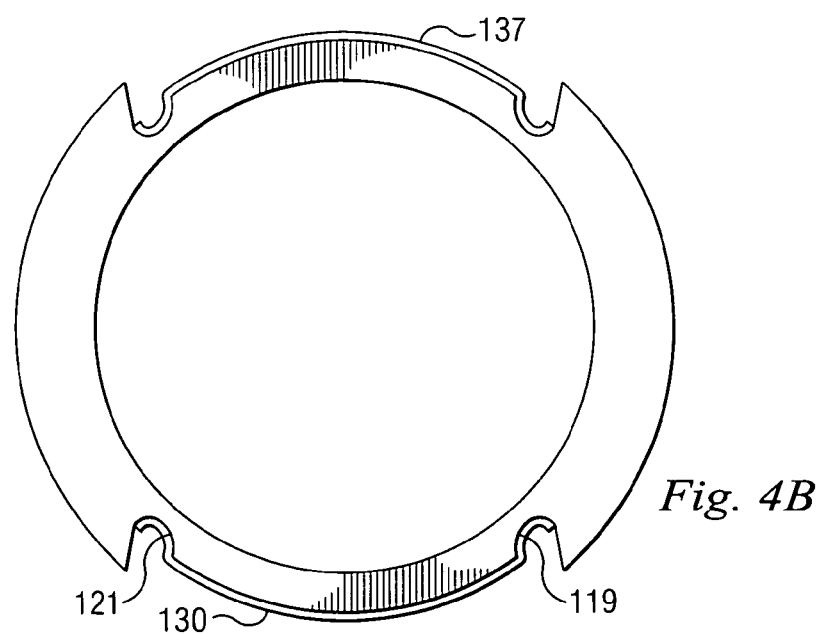
FIG. 4B is a top view of the implant of FIG. 4A.

An interference clip 130 is received on main body 110. Interference clip 130 includes a tool engagement opening 132 and a pair of retaining rails 134 and 136. Retaining rails 134 and 136 have an exterior convex surface substantially matching the diameter of semi-circular grooves 119 and 121. Retaining rails 134 and 136 are slidingly received along grooves 121 and 119, respectively. It will be appreciated that interference clip 130 may slide longitudinally along longitudinal axis L1 and is retained on main body by engagement of the rails 134 and 136 within groves 121 and 119. A second retaining clip 160 is also positioned on the device adjacent to wedge 150. The second retaining clip 160 also engages grooves 119 and 121, and may move longitudinally along the device. As shown in FIG. 4B, clip 137 is positioned on the opposite side on the device to be slidingly received within the longitudinal grooves. While only retaining clip 137 is shown, it will be appreciated that a lower clip similar to clip 160 is also present.

Referring now to FIG. 5B, clip 130 is shown in cross-section. Clip 130 has a leading end 131 of a first thickness and a trailing end 133 of a second thickness, the clip tapers between the smaller first thickness and the larger second thickness. It will be appreciated that the tapering wedge shape of clip 130 acts as a shim when received between unthreaded channel 114 and the unthreaded channel 190 of the bone engaging end. Clip 160 has a similar tapered shape with the leading tapered tip oriented toward the lower distal end of the device.

In a further embodiment, clips 130 and 160 have a greater longitudinal height and a substantially uniform thickness allowing the clips to slide freely in the space between unthreaded sections. The longitudinal height is sufficient such that when positioned past the end 142 of locking tab 140, the clip will extend longitudinally adjacent to at least a majority, if not all, of the threaded projections. It will be appreciated, that the upper interference clip 130 may positioned on one side of the main body, and the lower interference clip 160 may positioned on the opposite side of the main body to allow sufficient room for the clips in the central area of the main body in the unlocked condition.

Figure 3:
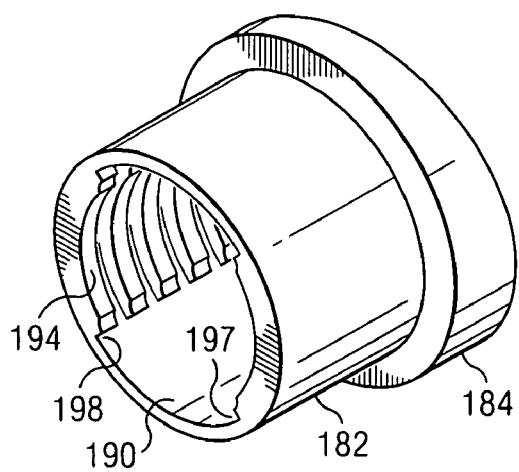
FIG. 3 in a perspective view of an end piece of the implant of FIG. 2A.

A pair of bone engaging sleeves are also provided for engagement with main body 110. Upper body engaging sleeve 180 includes a tubular barrel portion 182 and an enlarged flange area 184. Enlarged flange portion 184 includes a bone engaging surface 186 which in the illustrated embodiment includes a series of knurled projections for engagement with a boney surface. In the embodiments illustrated in FIGS. 2A and 3, the bone engaging end extends at a non-perpendicular angle with respect to the longitudinal axis L1. The angle may be any desired angle to substantially match the natural or restored angulation of lordosis or kyphosis between the remaining vertebral endplates. For example, each end plate may have 0, 3, or 6 degrees of angulation allowing the device to achieve 0 to 12 degrees of angulation between the remaining vertebrae. While a knurled surface has been shown for the purposes of illustration, in alternative embodiments the projections take the form of cones, blades, keels, fins, ridges, pegs or any other surface projection. Further, the surface 151 may be formed such that recesses in the surface create projections in a bone ingrowth type surface allowing bone to grow into the surface or to interdigitate with native bone on the endplates.

Bone engaging sleeve 180 is substantially tubular and includes a central passage 188. In a manner corresponding to the threaded and unthreaded portions of the main body 110, the bone engaging member 180 includes unthreaded channels 190 and 192 and threaded portions 194 and 196 each spaced at approximately 90 degree intervals around the internal surface. Disposed between the respective threaded and unthreaded portions, are a series of dovetail recesses 197, 198, 200 and 202. It will be appreciated that the size and shape of the dovetail recesses are formed to substantially mate with the dovetail projections of the main body 110 previously described. Moreover, the extent of the threaded portions 194 and 196 and the unthreaded portions 190 and 192 around the internal circumference of internal passage 188 substantially match the corresponding external structures disposed on main body 110.

The expandable device 100 is shown in a disassembled condition in FIG. 2a. In the illustrated embodiment, interference clips 130 and 160 have already been installed on the main body 110. It will be appreciated that upper bone engaging member 180 will be substantially aligned with threaded portions 194 and 196 aligned with the unthreaded channels 114 and 115 of main body 110. In this rotational alignment, upper bone engaging member 180 may be advanced toward the middle or center of the main body 110 along the longitudinal axis. In a similar manner, lower bone engaging member 220 is rotationally aligned such that the threaded portions are in substantial alignment with the unthreaded portions of main body 110. In this alignment, the lower bone engaging portion is longitudinally advanced towards the middle of main body 110. Each of the upper and lower bone engaging members may be rotated several degrees such that the internal threads of the bone engaging members engage the external threads of the main body. Interference clips 130 and 160 are held near the midline by wedges 140 and 150, respectively.

In this provisionally retained condition, the expandable implant 100 is positioned into the spinal segment in the space previously occupied by vertebral body V3 and the adjacent disks D2 and D3. Once the implant 100 has been properly positioned, the upper and lower bone engaging members are rotated about the longitudinal axis such that their angled faces are properly positioned against the adjacent vertebral bodies to obtain the desired amount of lordosis or kyphosis. It will be understood, that while the illustrated embodiments disclose angulation on the bone engaging surfaces, modified bone engaging end pieces may be provided having zero degrees of angulation up to or exceeding about 6 degrees of angulation. Within this range of end pieces, the total expanded construct may provide zero degrees of angulation (i.e. parallel orientation) between the endplates of the intact vertebra and up to or exceeding 12 degrees of angulation. Once the bone engaging portions have been properly oriented, a spreader or other type of distraction device is inserted to engage the large flange on each of the bone engaging members to urge them apart and into engagement with the intact vertebra. The central member is engaged by a tool (not shown) or by hand to substantially align the unthreaded channels with the threads of the bone engaging portions. In one aspect, the spreader engages each end piece to prevent rotation of the end pieces with respect to the central member. With the threads of the end pieces aligned with the unthreaded channels of the main body, the spreader is actuated to push the end pieces to slide along the longitudinal axis L1 to enlarge the height of the implant from its initial reduced height insertion configuration to its increased height spacing configuration, shown in FIG. 2B, that engages bone on opposing ends of the device.

Once the desired amount of expansion of the expandable device 100 has been obtained, and with the spreader still in place to hold the expansion, the main body 110 is engaged with a tool or by hand and rotated approximately 90 degrees to engage the threaded portions of the main body with the corresponding threaded portions of the respective upper and low bone engaging portions. In one embodiment, the spreader instrument includes a central cable and a winch spool to retract the cable. The end of the cable is removably coupled to the main body and at least partially wound around the main body. This attachment and winding can be performed before implantation into the body. After implantation and expansion of the implant, the cable winch is operated to retract the cable resulting in rotational movement of the main body. After this rotation, the spreading device and cable are removed and the expandable spacer 100 will maintain the height that was previously achieved during expansion of the spacer.

In order to inhibit rotation of the main body 110 and end piece 180 with respect to each other, the interference clip 130 is moved longitudinally away from the center of the device to a locked position as shown in FIG. 2B. In a similar manner, clip 160 is moved longitudinally towards the opposite end of the implant to maintain the end piece 220 in the engaged position with respect to main body 110. More specifically, a locking tool (not shown) such as a spreader is engaged with slot 132 on interference clip 130 and the corresponding slot 162 on interference clip 160. The locking tool then moves each of the retaining clips away from the middle of the main body and towards the distal ends, such that each clip passes over wedges 140 and 150 and ultimately passes beyond engagement shoulders 142 and 152, respectively. The clips continue to advance along grooves 119 and 121 distally until they are wedged at least in part between the unthreaded channel of the main body and the unthreaded channel of each of the bone engaging members.

In the illustrated embodiment, the interference clips have a tapered thickness such that under longitudinal force the reduced thickness leading ends are pressed into the space between the unthreaded channels. The engagement of the interference clip outer surface with the inner surface of the bone engaging end piece and opposing engagement of the clip inner surface with the outer surface of the main body firmly holds the clip in position. It is anticipated that the longitudinal force applied to the clips is such that once moved to the interference position, they may not be dislodged without a tool. Moreover, inadvertent movement of the clips out of the unthreaded channels is prevented by engagement with wedges 140 and 150. In the interference position between the unthreaded channel of the bone engaging portion and the unthreaded channel of the main body, the interference clips interrupt the threaded path of the threaded components to prevent the rotation of the main body with respect to the end portions and thereby maintain the threaded portions of the main body engaged with the threaded portions of the bone engaging end portions. Thus, the interference clips lock the device in its expanded condition.

In an alternative embodiment, the main body is substantially solid such that while it is telescopically received within the end portions, no material may be received within the main body. Moreover, while the main body has been shown as telescopically received within tubular upper and lower bone engaging members, it will be appreciated that in a further embodiment the respective configuration is inverted such that a shaft portion of the upper and lower bone engaging members is received within a hollow portion of a tubular main body. Moreover, while a substantially cylindrical structure has been shown for the purposes of illustration, in an alternative embodiment the tubular shapes may take the form of a rectangle, square, ellipse, diamond, oval, D-shape or any shape desired to conform and substantially match the adjacent bone or the bone structure that is being replaced. As a result, the definition of tubular is not intended to be limited to cylindrical but is instead intended to cover all components that may be utilized to reduce the present invention.

In an alternative embodiment, rather than have a separate retaining clip sliding along the longitudinal axis, at least one of the inner member or end pieces include one or more tabs that are moveable into the unthreaded channels to interfere with the rotation of the end piece with respect to the inner member once the tab is in the retained position. In one aspect, a plurality of locking tabs are formed to extend as ratchet members along the longitudinal axis. In one embodiment, the tabs are formed to resiliently snap into a locked position to prevent angular movement between the tubular end piece and the tubular main body. In an alternative embodiment, the tabs are formed such that a tool is used to deform the tab material to move it to a locked position. In still a further embodiment, the tubular endpieces are advanced by threaded engagement with the central tubular portion rather than the sliding longitudinal advancement discussed above. In this aspect, the interference clips are advanced along the longitudinal axis to retain the relative angular position of the components in a plurality of different configurations. In still a further embodiment, an elongated locking element is having a plurality of locking protrusions is provided. The locking element has a length that longitudinally extends through a plurality of support protrusions. In a first longitudinal position, the locking protrusions of the locking element are aligned with the support protrusions to allow movement between the main body and the end piece. In a second longitudinal position, the locking protrusions are aligned with spaces between the support protrusions to prevent movement between the main body and the end piece. The locking member is configured to move longitudinally between the first longitudinal position and the second longitudinal position.

While a portion of a helical threaded has been shown for the purpose of illustrating a type of locking protrusion, the disclosure encompasses any interlocking engagement structure that resists compressive forces applied along the longitudinal axis. For example, in one embodiment, the protrusions are ratchetings extending substantially perpendicular to the longitudinal axis L1 of the implant. In still further examples, but without limitation to alternative structures, alternative embodiments have protrusions taking the form of grooves, ridges, splines, tabs, flanges, fingers or any other type of projections.

While the present device has been described with respect to insertion between two vertebrae after removal of the intervening vertebrae and intervertebral disc, it is contemplated that the length of the device may be sized appropriate to span multiple vertebrae. Further, in an alternative embodiment, only a single endpiece is moveable along the main body such that the device telescopes in only one direction. Additionally, the device may find application in other orthopedic areas and the size and shape of the device may be made to substantially match the implantation site. For example, while the present embodiment has been illustrated as a substantially cylindrical device, it is contemplated that in certain spinal applications it is desirable that the device have a substantially D shaped cross-section as viewed from top to bottom such that the anterior portion of the device has an exterior convexly curved surface matching the anterior of the vertebral body while the posterior portion of the device is substantially flat or concave allowing it to be positioned closer to the spinal canal without protruding into the spinal canal.

Embodiments of the implant in whole or in part may be constructed of biocompatible materials of various types. Examples of implant materials include, but are not limited to, non-reinforced polymers, carbon-reinforced polymer composites, PEEK and PEEK composites, shape-memory alloys, titanium, titanium alloys, cobalt chrome alloys, stainless steel, ceramics and combinations thereof. If the trial instrument or implant is made from radiolucent material, radiographic markers can be located on the trial instrument or implant to provide the ability to monitor and determine radiographically or fluoroscopically the location of the body in the spinal disc space. In some embodiments, the implant or individual components of the implant are constructed of solid sections of bone or other tissues. In other embodiments, the implant is constructed of planks of bone that are assembled into a final configuration. The implant may be constructed of planks of bone that are assembled along horizontal or vertical planes through one or more longitudinal axes of the implant. In some embodiments, a cavity is cut or constructed through the implant. The cavity may be useful to contain grafting materials. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof. Examples of resorbable materials that may be used include, but are not limited to, polylactide, polyglycolide, tyrosine-derived polycarbonate, polyanhydride, polyorthoester, polyphosphazene, calcium phosphate, hydroxyapatite, bioactive glass, and combinations thereof. Implant may be solid, porous, spongy, perforated, drilled, and/or open.

In some circumstances, it is advantageous to pack all or a portion of the interior and/or periphery of the implant with a suitable osteogenetic material or therapeutic composition. Osteogenic materials include, without limitation, autograft, allograft, xenograft, demineralized bone, synthetic and natural bone graft substitutes, such as bioceramics and polymers, and osteoinductive factors. A separate carrier to hold materials within the device can also be used. These carriers can include collagen-based carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenetic compositions may include an effective amount of a bone morphogenetic protein, transforming growth factor $\beta 1$, insulin-like growth factor 1, platelet-derived growth factor, fibroblast growth factor, LIM mineralization protein (LMP), and combinations thereof or other therapeutic or infection resistant agents, separately or held within a suitable carrier material. A technique of an embodiment of the invention is to first pack the interior of an unexpanded implant with material and then place one or both end members if desired. Upon expanding the device to an expanded state such as is shown in FIG. 2B, material may additionally be placed through the opening 125. Placement may be accomplished directly or with the aid of an injection or transfer device of any effective type.

Access to the surgical site may be through any surgical approach that will allow adequate visualization and/or manipulation of the skeletal structures. Example surgical approaches include, but are not limited to, any one or combination of anterior, antero-lateral, posterior, postero-lateral, transforaminal, and/or far lateral approaches. Implant insertion can occur through a single pathway or through multiple pathways, or through multiple pathways to multiple levels of the spinal column. Minimally invasive techniques employing instruments and implants are also contemplated. It is understood that all spatial references, such as "top," "inner," "outer," "bottom," "left," "right," "anterior," "posterior," "superior," "inferior," "medial," "lateral," "upper," and "lower" are for illustrative purposes only and can be varied within the scope of the disclosure.

FIG. 1 illustrates four vertebrae, V1-V4, of a typical lumbar spine and three spinal discs, D1-D3. While embodiments of the invention may be applied to the lumbar spinal region, embodiments may also be applied to the cervical or thoracic spine or between other skeletal structures.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A medical implant expandable along a longitudinal axis and for supporting skeletal structures comprising:
   a first tubular member with a connection end extending along the longitudinal axis and an opposite skeletal interface end, the connection end of the first tubular member including an area with protrusions and an area without protrusions;
   a second tubular member with a connection end extending along the longitudinal axis configured to engage with the connection end of the first tubular member, the second tubular member having an opposite end opposite from the connection end of the second tubular member, the connection end of the second tubular member including an area with protrusions and an area without protrusions, wherein in a first angular relationship between the first and second tubular members, the area with protrusions of the first tubular member slides longitudinally along the area without protrusions of the second tubular member, and in a second angular relationship the protrusions of the first and second tubular members engage to prevent longitudinal sliding between the first and second tubular members; and
   a non-threaded interference mechanism configured to slide longitudinally between said first tubular member and said second tubular member to enter at least a portion of the area without protrusions of the first tubular member to prevent angular movement between the first tubular member and the second tubular member.

2. The medical implant of claim 1 wherein the first and second tubular members are substantially round in cross-section.

3. The medical implant of claim 1 wherein the protrusions on the first and second tubular members are threads.

4. The medical implant of claim 1 wherein the protrusions on the first and second tubular members are ratchetings substantially perpendicular to a longitudinal axis of the implant.

5. The medical implant of claim 1 wherein the protrusions on the first tubular member are located on opposite interior sidewalls of the first tubular member in segments extending across approximately one quarter of the interior sidewalls respectively.

6. The medical implant of claim 1 wherein the protrusions on the second tubular member are located on opposite exterior sidewalls of the second tubular member in segments extending across approximately one quarter of the exterior sidewalls respectively.

7. The medical implant of claim 1 wherein the interference mechanism slides along a portion of the second tubular member to enter the at least a portion of the area without protrusions of the first tubular member to prevent angular movement between the first tubular member and the second tubular member.

8. The medical implant of claim 7, wherein said interference mechanism includes a leading end having a first height, a trailing end having a second height and a sloping surface extending between the leading and trailing ends, the first height less than the second height, and wherein at least a portion of the leading end enters the at least a portion of the area without protrusions of the first tubular member to prevent angular movement.

9. The medical implant of claim 1 wherein the second tubular member includes a locking tab for releasably holding the interference mechanism in place to prevent angular movement between the first tubular member and the second tubular member.

10. The medical implant of claim 9 wherein the locking tab is biased to block movement of the interference mechanism when the interference mechanism is in position to prevent angular movement between the first tubular member and the second tubular member.

11. The medical implant of claim 1 wherein the second tubular member includes a first locking tab for releasably holding a first interference mechanism in place on a first exterior side of the second tubular member and a second locking tab for releasably holding a second interference mechanism in place on a second exterior side of the second tubular member, one or both of the first and second interference mechanisms to prevent angular movement between the first tubular member and the second tubular member.

12. The medical implant of claim 1 further comprising a third tubular member with a connection end configured to engage with the opposite end of the second tubular member, the third tubular member having an opposite skeletal interface end, the connection end of the third tubular member including an area with protrusions and an area without protrusions, wherein in a third angular relationship between the second and third tubular members, the area with protrusions of the third tubular member slides longitudinally along the area without protrusions of the second tubular member, and in a fourth angular relationship the protrusions of the second and third tubular members engage to prevent longitudinal sliding between the second and third tubular members.

13. The medical implant of claim 12 wherein the second tubular member includes a first, upper locking tab for releasably holding a first interference mechanism in place on a first exterior side of the second tubular member, a first, lower locking tab for releasably holding a first interference mechanism in place on a first exterior side of the second tubular member, a second, upper locking tab for releasably holding a second interference mechanism in place on a second exterior side of the second tubular member, and a second, lower locking tab for releasably holding a second interference mechanism in place on a second exterior side of the second tubular member, one or both of the first and second interference mechanisms to prevent angular movement between the first tubular member and the second tubular member or between the third tubular member and the second tubular member.

14. An expandable medical implant for supporting skeletal structures comprising:
a first tubular member with a connection end and an opposite skeletal interface end;
a second tubular member with a connection end configured to engage with the connection end of the first tubular member, the second tubular member having an opposite end opposite from the connection end of the second tubular member; and
a non-threaded interference mechanism with a first position that allows movement between the first tubular member and the second tubular member and a second position longitudinally spaced from the first position that prevents movement between the first tubular member and the second tubular member;
wherein the connection ends of the first tubular member and the second tubular member are configured to allow sliding translation between the first tubular member and the second tubular member when in a first angular relationship and to prevent sliding translation when in a second angular relationship.

15. The expandable medical implant of claim 14 wherein the interference mechanism prevents angular movement between the first tubular member and the second tubular member when in the second position.

16. The expandable medical implant of claim 14 wherein the first and second tubular members are substantially round in cross-section.

17. The expandable medical implant of claim 14 wherein the interference mechanism slides along a portion of the second tubular member to the second position to prevent angular movement between the first tubular member and the second tubular member.

18. The expandable medical implant of claim 14 wherein the second tubular member includes a locking tab for releasably holding the interference mechanism in the second position.

19. The expandable medical implant of claim 18 wherein the locking tab is biased to block movement of the interference mechanism when the interference mechanism is in the second position.

20. The expandable medical implant of claim 14 further comprising a third tubular member with a connection end configured to engage with the opposite end of the second tubular member, the third tubular member having an opposite skeletal interface end.

21. A medical implant expandable along a longitudinal axis and for supporting skeletal structures comprising:
a first tubular member with a first connection end and an opposite skeletal interface end, the first connection end comprising an inner surface having a first side and a second side, the first side comprising an area with protrusions and the second side comprising an area without protrusions;
a second tubular member with a second connection end configured to engage with the first connection end, the second connection end comprising an outer surface having a third side and a fourth side, the third side comprising an area with protrusions and the fourth side comprising an area without protrusions, wherein the area of the fourth side without protrusions further comprises a channel;
wherein a first angular relationship between the first and second connection ends, the first side of the first connection end slides longitudinally along the channel of the fourth side of the second connection end, and in a second angular relationship the first side of the first connection end engages with the third side of the second connection end to prevent longitudinal sliding between the first and second tubular members; and
a non-threaded interference mechanism configured to slide longitudinally along the channel of the fourth side of second connection end, wherein the fourth side of the second connection end further comprises a locking tab for releasably holding the interference mechanism in place to prevent angular movement between the first tubular member and the second tubular member.

22. A medical implant expandable along a longitudinal axis and for supporting skeletal structures comprising:
a first tubular member with a first connection end and an opposite skeletal interface end, the first connection end comprising an inner surface having a first side and a second side, the first side comprising an area with protrusions and the second side comprising an area without protrusions;
a second tubular member with a second connection end configured to be received within a portion of the first connection end, the second tubular member having a third connection end opposite from the second connection end of the second tubular member, the second connection end comprising an outer surface having a third side and a fourth side, the third side comprising an area with protrusions and the fourth side comprising an area without protrusions, wherein the area of the fourth side without protrusions further comprises a channel;

wherein in a first angular relationship between the first and second connection ends, the first side of the first connection end slides longitudinally along the channel of the fourth side of the second connection end, and in a second angular relationship the first side of the first connection end engages with the third side of the second connection end to prevent longitudinal sliding between the first and second tubular members; and an interference mechanism having an interference inner surface and an interference outer surface, the interference mechanism configured to slide longitudinally along the channel of the second connection end with the interference inner surface facing the fourth side and the outer interference surface facing the second side to engage an area between the fourth side of the second connection end and the second side of the first connection end, wherein the engaged interference mechanism prevents angular movement between the first tubular member and the second tubular member.

23. The medical implant of claim 22 wherein the second tubular member includes a locking tab for releasably holding the interference mechanism in place to prevent angular movement between the first tubular member and the second tubular member.

24. The medical implant of claim 22 wherein the interference mechanism is mounted on the fourth side of the second connection end.

25. The medical implant of claim 24 wherein the interference mechanism extends across the channel of the fourth side of the second connection end.

26. The medical implant of claim 22 further comprising a third tubular member with a fourth connection end configured to engage with the third connection end of the second tubular member, the third connection end of the second tubular member including an area with protrusions and an area without protrusions, the fourth connection end of the third tubular member including an area with protrusions and an area without protrusions, wherein in a third angular relationship between the second and third tubular members, the area with protrusions of the fourth connection end slides longitudinally along the area without protrusions of the third connection end, and in a fourth angular relationship the protrusions of the third and fourth connection ends engage to prevent longitudinal sliding between the second and third tubular members.

* * * * *